United States Patent
Schapp et al.

(10) Patent No.: US 7,893,290 B1
(45) Date of Patent: Feb. 22, 2011

(54) PROCESS FOR THE PREPARATION OF BIS(PENTADIENYL)-COMPLEXES OF IRON GROUP METALS

(75) Inventors: Jan Schapp, Wessling (DE); Kevin King, Torrance, CA (US); Stephen Jeffery, Huntington Beach, CA (US)

(73) Assignee: W.C. Heraeus GmbH, Hanau (DE)

( * ) Notice: Subject to any disclaimer, the term of this patent is extended or adjusted under 35 U.S.C. 154(b) by 0 days.

(21) Appl. No.: 12/758,890

(22) Filed: Apr. 13, 2010

(51) Int. Cl.
*C07F 17/00* (2006.01)
*C07F 15/00* (2006.01)

(52) U.S. Cl. .................. 556/136; 556/140; 556/143

(58) Field of Classification Search .................. 556/136, 556/140, 143
See application file for complete search history.

(56) References Cited

U.S. PATENT DOCUMENTS 6,002,036 A   12/1999   Kadokura
6,642,402 B2  11/2003   Voll Barclay et al.

*Primary Examiner*—Porfirio Nazario Gonzalez
(74) *Attorney, Agent, or Firm*—Panitch Schwarze Belisario & Nadel LLP

(57) ABSTRACT

A method for preparing organometallic complexes of the general formula (I):

$$M(RPD)_2 \qquad (I)$$

in which M may be iron, ruthenium, or osmium, R is hydrogen or an alkyl group having about 1 to 4 carbon atoms, and PD is a cyclic or open chain dienyl system that is known to form a sandwich type complex is provided. The complexes having formula (I) have a metal purity of at least about 99.99%. The method involves reacting a M(III) trichloride hydrate with an HRPD compound and at least one reducing metal, such as aluminum, in an alcohol solvent.

12 Claims, No Drawings

PROCESS FOR THE PREPARATION OF BIS(PENTADIENYL)-COMPLEXES OF IRON GROUP METALS

BACKGROUND OF THE INVENTION

The invention relates to a method for the preparation of bis(dienyl)complexes of iron group metals, such as bis(pentadienyl) complexes of iron group metals.

M(RPD)$_2$ type organometallic complexes, in which M represents iron, ruthenium, or osmium; R represents hydrogen or an alkyl group; and PD may be a cyclic or open chain dienyl system that forms a sandwich type complex, are commonly used in processes relating to thin film formation. For example, ruthenium thin films may be used in semiconductor manufacture, where resistive or conductive layers are desired, as decorative coatings on ceramics, and in resistively heated surfaces, as in automotive windows. The electronic component literature describes conductive film formation and resistive film formation via chemical vapour deposition (CVD). For electronic devices, high purity raw materials are imperative for producing operational parts in high yield.

In the processes described in U.S. Pat. Nos. 6,002,036 and 6,642,402 for forming bis(dienyl)ruthenium complexes, zinc and magnesium, respectively, are utilized as reducing metals. Using Zn or Mg in the reaction, however, can form pentadienyl-Zn and pentadienyl-Mg impurities. Although the described prior art generally avoids water in the reaction, Kadokura (U.S. Pat. No. 6,002,036) suggests that trace water from the reactant RuCl$_3$ hydrate is adequate to decompose any Zn(EtCp)$_2$ that may form. However, there is no indication as to how much water is supplied by the Ru salt. Metal hydrates are generally non-stoichiometric, and typically, FeCl$_3$, RuCl$_3$, and OsCl$_3$ hydrate salts vary in their water content. Accordingly, the water of hydration may be insufficient to decompose the unwanted metal pentadienyl compounds, and such impurities may still be present in the prior art complexes.

It would thus be desirable to produce the above-described M(RPD)$_2$ complexes in high yields while ensuring that base metal impurities are minimized.

BRIEF SUMMARY OF THE INVENTION

The invention relates to method of preparing an organometallic complex of formula (I):

M(RPD)$_2$          (I)

wherein M=iron, ruthenium, or osmium; R=H or an alkyl group having about 1 to 4 carbon atoms; and PD=a cyclic or open chain dienyl system that forms a sandwich type complex, and wherein the compound having formula (I) has a metal purity of at least about 99.99%. The method comprises reacting a M(III) trichloride hydrate and a HRPD compound with at least one reducing metal selected from the group consisting of Al, Ga, In, Th, Cd, Hg, Li, Na, Ti, V Cr, Mn, Pb, Ni, Ca, and Cu in an alcohol solvent.

DETAILED DESCRIPTION OF THE INVENTION

The invention relates to a method of preparing organometallic complexes of the general formula (I):

M(RPD)$_2$          (I)

In formula (I), M is a metal selected from iron, ruthenium, or osmium, and is preferably ruthenium. R may be hydrogen or a C$_{1-4}$-alkyl group, such as CH$_3$ (methyl), C$_2$H$_5$ (ethyl), C$_3$H$_7$ (n-propyl or isopropyl), or C$_4$H$_9$ (n-butyl, isobutyl, or tert-butyl)). PD represents a cyclic or open chain dienyl system (ligand) that may form a sandwich type complex. Suitable dienyl systems are known in the art and include, for example, optionally substituted cyclic pentadienyl, cyclopentadienyl, indenyl, tetrahydroindenyl, fluorenyl, and octahydrofluorenyl ligands. A preferred PD ligand is optionally substituted cyclic pentadienyl that may have at least one C$_1$-C$_4$ alkyl side chain, such as two methyl side chains.

The organometallic complexes having formula (I) that are prepared according to the invention are substantially free of base metal impurities. Base metals are commonly known as easily oxidizable metals which dissolve in hydrochloric acid and release hydrogen. For example, Fe, Ni, Pb, Zn, and sometimes Cu are conventionally regarded as base metals. High metal purity is imperative for the high yield manufacture of operational electronic devices. The inventive complexes preferably have a metal purity of at least 99.99% (4N), more preferably a metal purity as high as 99.995%. In other words, the total metal impurities comprise less than 100 ppm of the weight of the complex having formula (I), or less than 50 ppm in a preferred embodiment. The term "metal impurity" may be understood to describe the amount of trace metal elements other than Pt group elements (such as B, Na, and Fe) that are present in the complex.

Preferred organometallic complexes having formula (I) that may be prepared according to the invention include bis (ethylcyclopentadienyl)ruthenium(II) and bis(2,4-dimethylpentadienyl)ruthenium(II), as shown in FIGS. 1 and 2 respectively.

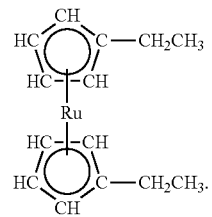

Fig. 1

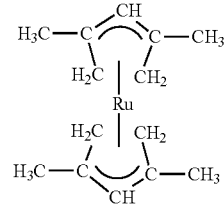

Fig. 2

The process for preparing organometallic complexes of formula (I) comprises reacting a M(III) trichloride hydrate and a HRPD compound with at least one reducing metal, preferably in powder form, in an alcohol solvent. For example, bis(ethylcyclopentadienyl)ruthenium(II) may be prepared by reacting RuCl$_3$ hydrate with ethylcyclopentadiene (HEtCp) and a reducing metal.

The alcohol solvent is preferably a C$_1$-C$_6$ alcohol, such as methanol, ethanol, isopropanol, n-butanol, t-butanol, n-pentanol, or n-hexanol. Ethanol is a particularly preferred solvent.

Preferred reducing metals include, without limitation, Al, Ga, In, Th, Cd, Hg, Li, Na, Ti, V Cr, Mn, Pb, Ni, Ca, and Cu. The reducing metal preferably has a purity of about 99% or greater and a particle size of about 75 microns or less. However, it is also within the scope of the invention to utilize reducing metals with other sizes and purities. It is also within the scope of the invention to include more than one reducing metal in the reaction mixture. More preferably, the reducing metal is aluminum because it is particularly effective for facilitating reactions between $RuCl_3$ salts and pentadienes in alcohol to yield cyclic and open chain ruthenocenes. As previously described, in prior art processes using Mg or Zn as a reducing agent, pentadienyl-Zn and pentadienyl-Mg impurities may be problematic and difficult to remove. However, because the analogous pentadienyl-Al compound is highly unstable, it is not expected to be present as an impurity in the reaction mixture according to the invention.

The reaction is preferably performed under an inert atmosphere, such as argon, at slightly above atmospheric pressure (such as 1-2 inches of water). The reaction is preferably performed at a reduced temperature, such as about −20° C. or below, and allowed to react slowly and warm to room temperature over about 12-18 hours. It is important that the reaction be performed at low temperature because an exothermic reaction may cause undesirable polymerization of the HRPD ligand. The actual time needed to complete the reaction may be determined on a case-by-case basis depending on the specific reactants.

The reaction of M(III) trichloride hydrate, HRPD, and reducing metal may result in various byproducts, such as HRPD-dimer, PD-M-RPD, and $M'(RPD)_x$, in which M' represents a metal other than M, such as a reducing metal or semi-metal. M' may be the reducing metal used in the reaction or may result from an impurity in one of the starting materials, and x is an integer determined by the valence of M'. For example, M' may be the reactant Al, but may also be Na, K, B, Zn, Fe, or Mg. In prior art processes using Mg or Zn as a reducing metal, $ZnRPD_2$ and $MgRDP_2$ impurities may be formed, and expensive vacuum distillation equipment is required to separate such potential contaminant byproducts from the desired organometallic complex. However, it has been found that water added to the reaction will readily decompose any $Al(RPD)_3$ to a non-organic soluble material that may be easily removed by filtration prior to purification of the desired organometallic complex. Analogous Zn and Mg impurities would not be so easily removable.

Accordingly, in order to eliminate undesirable $M'(RPD)_x$ byproducts, the method preferably includes adding to the reaction mixture an amount of water sufficient to completely decompose any $M'(RPD)_x$ complexes. This water will supplement any waters of hydration that are present in the reaction mixture from the metal salt reactant and will react with the reactive $Al(RPD)_3$ or other $M'(RPD)_x$ species that may form. The water is preferably added in at least a 100% molar excess with respect to the change in valency of the reducing metal reactant to ensure that all $M'(RPD)_x$ compounds are completely decomposed. For example, one mole of $Al^{3+}$ would require 6 moles of water. Such an excess will ensure that the $M'(RPD)_x$ species formed from both the reducing metal reactant and the impurities will be decomposed. That is, trace base metals are very small in quantity compared to the Al and M (Ru, Fe, Os) present, and the amount of water added is adequate to decompose any $Al(RPD)_3$ according to the reaction $3H_2O+Al(RPD)_3 \rightarrow Al(OH)_3+3HRPD$. It is preferable not to rely on the water of hydration in the Fe, Ru, or Os trichlorohydrate reactant to decompose any $Zn(RPD)_2$ or $Mg(RPD)_2$ or $Al(RPD)_3$ byproducts. Rather, adding excess water ensures that the unwanted metallocene species will be completely destroyed.

Following reaction of the metal trichloride hydrate, HRPD, and reducing metal, the organometallic metal dienyl complex may be purified by standard techniques. For example, the reaction mixture may be distilled under reduced pressure, such as by utilizing a standard distillation column. Preferred distillation conditions include a pot temperature of about 150° C. and a pressure of about 0.2 mmHg. However, the specific distillation conditions may be determined experimentally on a case-by-case basis depending on the specific reactants and product.

According to the process of the present invention, yields of up to 95% of the complex having formula (I) may be attained, making the process desirable for industrial applications. The metal purity of the complexes may be determined by ICP-MS (Ion Coupled Plasma-Mass Spectrometry) or other analytic methods. Because the most frequently occurring impurities are removed during the process, the resulting products have very high metal purity, as high as 99.995%.

The invention will now be illustrated in conjunction with the following, non-limiting example. Parts and percentages are by weight unless otherwise indicated.

EXAMPLE

Preparation of Bis(EtCp)Ru (II) from $RuCl_3$ hydrate+HEtCp

Into an argon flushed 12 L 3 neck round bottom flask equipped with overhead stirring, 3.5 L of ethanol, 671 g of HEtCp (dimer, commercially available from Sigma-Aldrich) and 144 g of aluminum powder (particle size less than 75 microns, purity 99+%, commercially available from Sigma-Aldrich) were charged. In a separate argon flushed flask, 415 g $RuCl_3$ hydrate (manufactured by W. C. Heraeus, Santa Fe Springs Calif.), 625 mL water and 1876 mL ethanol were combined. The contents of the 12 L flask were chilled to below −20° C. (253 K) and a slow steady addition of the ruthenium solution was commenced and continued for 3 hours. After all of the ruthenium solution had been added, the reaction was allowed to slowly warm back to room temperature. After completion, the reaction appeared to be a gray colored slurry.

The slurry was filtered under inert gas, concentrated to oily solids, and extracted into hexanes. The hexanes extract was concentrated to an amber oil. Subsequent high vacuum distillation yielded 490 g of the desired product in >80% purity (HEtCp-dimer and Cp-Ru-EtCp comprised about 8% of the product mixture). A base metal analysis by ICP-MS of the sample showed only B (1.8 ppm) and Na (0.5 ppm) at levels greater than or equal to 0.5 ppm. All other metals were present in amounts of less than 0.5 ppm. In particular, the concentration of Fe, a common impurity in Ru, was <0.5 ppm. Accordingly, the product had a metal purity as high as 99.995%.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of preparing an organometallic complex of formula (I):

$$M(RPD)_2 \qquad (I)$$

wherein M=iron, ruthenium, or osmium; R=H or an alkyl group having about 1 to 4 carbon atoms; PD=a cyclic or open chain dienyl system that forms a sandwich type complex, and wherein the complex having formula (I) has a metal purity of at least about 99.99%; the method comprising reacting a M(III) trichloride hydrate and an HRPD compound with at least one reducing metal selected from the group consisting of Al, Ga, In, Th, Cd, Hg, Li, Na, Ti, V Cr, Mn, Pb, Ni, Ca, and Cu in an alcohol solvent.

2. The method according to claim 1, wherein the reducing metal is aluminum.

3. The method according to claim 1, wherein the reducing metal is in a form of a powder.

4. The method according to claim 1, wherein at least one M'(RPD)$_x$ compound is formed as a byproduct, wherein M' is a metal other than M and x is an integer determined by a valence of M', the method further comprising adding to the reaction water in an amount effective to completely decompose the at least one M'(RPD)$_x$ compound.

5. The method according to claim 4, wherein M' is selecting from the group consisting of Zn, Mg, Fe, and Al.

6. The method according to claim 1, further comprising purifying the organometallic complex having formula (I) by distilling under reduced pressure.

7. The method according to claim 6, wherein the distillation is performed with a pot temperature of about 150° C. and a pressure of about 0.2 mmHg.

8. The method according to claim 1, wherein PD is an optionally substituted non-cyclic or cyclic pentadienyl ligand.

9. The method according to claim 8, wherein PD is a non-cyclic or cyclic pentadienyl having from about one to about five side chains.

10. The method according to claim 1, wherein PD is ethylcyclopentadienyl or 2,4-dimethylpentadienyl.

11. The method according to claim 1, wherein the organometallic complex having formula (I) is bis(ethylcyclopentadienyl)ruthenium(II):

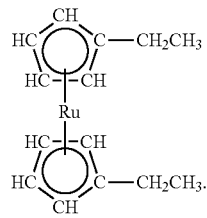

12. The method according to claim 1, wherein the organometallic complex having formula (I) is bis(2,4-dimethylpentadienyl)ruthenium(II):

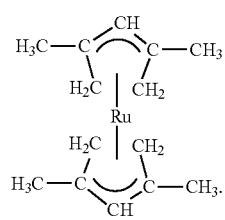

* * * * *